United States Patent
Belliotti et al.

(10) Patent No.: US 6,436,974 B1
(45) Date of Patent: Aug. 20, 2002

(54) AMINO HETEROCYCLES USEFUL AS PHARMACEUTICAL AGENTS

(75) Inventors: Thomas Richard Belliotti, Saline; Andrew John Thorpe; David Juergen Wustrow, both of Ann Arbor, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/980,187

(22) PCT Filed: Apr. 28, 2000

(86) PCT No.: PCT/US00/11399

§ 371 (c)(1),
(2), (4) Date: Nov. 30, 2001

(87) PCT Pub. No.: WO00/73300

PCT Pub. Date: Dec. 7, 2000

Related U.S. Application Data

(60) Provisional application No. 60/137,096, filed on Jun. 2, 1999.

(51) Int. Cl.[7] ............ A61K 31/4245; A61P 25/22; C07D 413/04
(52) U.S. Cl. ............ 514/364; 514/381; 548/132; 548/254
(58) Field of Search ............ 548/132, 254; 514/381, 364

(56) References Cited

U.S. PATENT DOCUMENTS

| | | | | |
|---|---|---|---|---|
| 5,066,662 A | * | 11/1991 | Hobbs et al. | 526/422 |
| 5,356,902 A | | 10/1994 | Ornstein | 514/307 |
| 5,446,051 A | | 8/1995 | Orstein | 514/307 |
| 5,510,381 A | | 4/1996 | Pande | 514/561 |

FOREIGN PATENT DOCUMENTS

| | | |
|---|---|---|
| EP | 0402056 | 12/1990 |
| GB | 1354554 | 5/1974 |

OTHER PUBLICATIONS

PCT International Search Report PCT/US00/11399.

* cited by examiner

Primary Examiner—Robert W. Ramsuer
Assistant Examiner—Jennifer C. Murphy
(74) Attorney, Agent, or Firm—Elizabeth M. Anderson; David R. Kurlandsky; Charles W. Ashbrook

(57) ABSTRACT

The instant invention is a novel series of amino heterocycles useful in the treatment of epilepsy, faintness attacks, hypokinesia, cranial disorders, neurodegenerative disorders, depression, anxiety, panic, pain, neuropathological disorders, and sleep disorders. Processes for the preparation and intermediates useful in the preparation are also disclosed.

19 Claims, No Drawings

AMINO HETEROCYCLES USEFUL AS PHARMACEUTICAL AGENTS

This application is a 371 of PCT/US00/1399 filed Apr. 28, 2000, which claims benefit of Ser. No. 60/137,096 filed Jun. 2, 1999.

SUMMARY OF THE INVENTION

The instant invention is a compound of Formula I

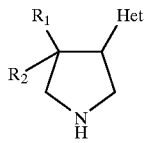

wherein $R_1$, $R_2$, and Het are as defined below.

Preferred compounds of the invention as those of Formula I wherein $R_1$ and $R_2$ are each independently hydrogen or a straight or branched alkyl of from 3 to 8 carbon atoms; and Het is

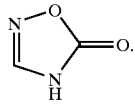

Other preferred compounds of the invention are those of Formula I wherein $R_1$ and $R_2$ are taken together with the carbon to which they are attached to form a carbocyclic ring of from 3 to 8 carbon atoms; and Het is

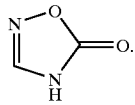

Still other preferred compounds of the invention are those of Formula I wherein $R_1$ and $R_2$ are each independently hydrogen or a straight or branched alkyl of from 3 to 8 carbon atoms; and Het is

Still other preferred compounds of the invention are those of Formula I wherein $R_1$ and $R_2$ are taken together with the carbon atom to which they are attached to form a carbocyclic ring of from 3 to 8 carbon atoms; and Het is

More preferred compounds are selected from:
trans 3-(4-Isobutyl-pyrrolidin-3-yl)-4H-[1,2,4]oxadiazol-5-one;
cis 3-(4-Isobutyl-pyrrolidin-3-yl)-4H-[1,2,4]oxadiazol-5-one;
trans 5-(4-Isobutyl-pyrrolidin-3-yl)-1H-tetrazole;
cis 5-(4-Isobutyl-pyrrolidin-3-yl)-1H-tetrazole;
3-(2-Aza-spiro[4.5]dec-4-yl)-4H-[1,2,4]oxadiazol-5-one; and
4-(1H-Tetrazol-5-yl)-2-aza-spiro[4.5]decane.

The instant invention is also pharmaceutical compositions comprising a therapeutically effective amount of one or more compounds of Formula I and a pharmaceutically acceptable carrier.

The compounds of the invention are agents in the treatment of epilepsy, faintness attacks, hypokinesia, cranial disorders, neurodegenerative disorders, depression, anxiety, panic, pain, neuropathological disorders, and sleep disorders.

DETAILED DESCRIPTION OF THE INVENTION

The instant invention is a novel series of amino heterocycles of Formula I

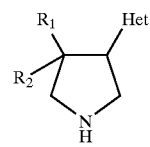

or a pharmaceutically acceptable salt thereof wherein:
$R_1$ and $R_2$ are each independently hydrogen or a straight or branched alkyl of from 3 to 8 carbon atoms; or
$R_1$ and $R_2$ are taken together to form a carbocyclic ring of from 3 to 8 carbon atoms;
Het is

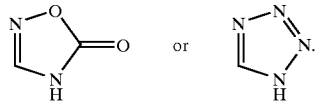

Since amino acids are amphoteric, pharmacologically compatible salts can be salts of appropriate inorganic or organic acids, for example, hydrochloric, sulphuric, phosphoric, acetic, oxalic, lactic, citric, malic, salicylic, malonic, maleic, succinic, methanesulfonic acid, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The terms used to define the invention are as described below.

The term alkyl is a straight or branched group of from 3 to 8 carbon atoms including but not limited to propyl, n-propyl, isopropyl, butyl, 2-butyl, tert-butyl, pentyl, hexyl, and n-hexyl, heptyl, and octyl except as where otherwise stated.

The cycloalkyl groups are from 3 to 8 carbons and are cyclopropyl, cyclobutyl, cyclopentyl, cyclohexyl, cycloheptyl, and cyclooctyl unless otherwise stated.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The radioligand binding assay using [$^3$H]gabapentin and the $\alpha_2\delta$ subunit derived from porcine brain tissue was used ("The Novel Anti-convulsant Drug, Gabapentin, Binds to the $\alpha_2\delta$ Subunit of a Calcium Channel," Gee N.S., et al., *J. Biol. Chem.*, 1996;271(10):5768–5776).

The compounds of the invention show good binding affinity to the $\alpha_2\delta$ subunit. Gabapentin (Neurontin®) is about 0.10 to 0.12 $\mu$M in this assay. Since the compounds of the instant invention also bind to the subunit, they are expected to exhibit pharmacologic properties comparable to gabapentin. For example, as agents for anxiety and pain.

Biological Activity

Binding to the $\alpha_2\delta$ subunit for the final products are expected to be in the range of >10 $\mu$M to 43 nM. In the carageenan induced hyperalgesia model, maximal possible effects observed ranged from inactivity to 83% of the maximal possible effect. When compared to the activity of a reference agent, in this case pregabalin, activities were observed in the Vogel conflict assay of 0% to 53% of the activity of the standard.

The compounds of the invention will treat disorders, for example, Alzheimer's disease, Huntington's disease, Parkinson's disease, Amyotrophic Lateral Sclerosis, epilepsy, and pain.

Pain refers to acute as well as chronic pain.

Acute pain is usually short-lived and is associated with hyperactivity of the sympathetic nervous system. Examples are postoperative pain and allodynia.

Chronic pain is usually defined as pain persisting from 3 to 6 months and includes somatogenic pains and psychogenic pains. Other pain is nociceptive.

Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

Other incidents are head trauma, spinal cord trauma, or injury from general anoxia, hypoxia, hypoglycemia, and hypotension as well as similar injuries seen during procedures from embole, hyperfusion, and hypoxia.

The compounds of the instant invention will be useful in gastrointestinal disorders, for example, irritable bowel syndrome (IBS).

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

The compounds of the instant invention are expected to be useful in the treatment of anxiety and of panic as demonstrated by means of standard pharmacological procedures.

MATERIAL AND METHODS

Carrageenin-Induced Hyperalgesia

Nociceptive pressure thresholds were measured in the rat paw pressure test using an analgesymeter (Randall-Sellitto Method: Randall L. O., Sellitto J. J., A method for measurement of analgesic activity on inflamed tissue. *Arch. Int. Pharmacodyn*, 4:409419 (1957)). Male Sprague-Dawley rats (70–90 g) were trained on this apparatus before the test day. Pressure was gradually applied to the hind paw of each rat and nociceptive thresholds were determiined as the pressure (g) required to elicit paw withdrawal. A cutoff point of 250 g was used to prevent any tissue damage to the paw. On the test day, two to three baseline measurements were taken before animals were administered 100 $\mu$L of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg/kg, s.c.), morphine (3 mg/kg, s.c.), or saline at 3.5 hours after carrageenin and nociceptive thresholds were examined at 4, 4.5,and 5 hours post carrageenin.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., Exploration of mice in a black and white box: validation as a model of anxiety. *Pharmacol. Biochem. Behav.*, 32:777–785 (1989)).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., Effects of anxiolytic and anxiogenic drugs on exploratory activity in a simple model of anxiety in mice. *Neuropharmacol.*, 28:901–905 (1989)).

Rat Elevated X-Maze

A standard elevated X-maze (Handley S. L., et al., Effects of alpha-adrenoceptor agonists and antagonists in a maze-exploration model of fear—motivated behavior. Naunyn-Schiedeberg's Arch. Pharmacol., 327:1–5 (1984)), was automated as previously described (Field, et al., Automation of the rat elevated X-maze test of anxiety. Br. J. Pharmacol., 102(Suppl):304P (1991)). The animals are placed on the center of the X-maze facing one of the open arms. For determining anxiolytic effects the entries and time spent on the end half sections of the open arms is measured during the 5-minute test period (Costall, et al., Use of the elevated plus maze to assess anxiolytic potential in the rat. *Br. J. Pharmacol.*, 96(Suppl):312P (1989)).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

The compounds of the instant invention are also expected to be useful in the treatment of pain and phobic disorders (*Am. J. Pain Manag.*, 5:7–9 (1995)).

The compounds of the instant invention are also expected to be useful in treating the symptoms of manic, acute or chronic, single upside, or recurring depression. They are also expected to be useful in treating and/or preventing bipolar disorder (U.S. Pat. No. 5,510,381).

TNBS-Induced Chronic Visceral Allodynia In Rats

Injections of trinitrobenzene sulfonic (TNBS) into the colon have been found to induce chronic colitis. In human, digestive disorders are often associated with visceral pain. In these pathologies. the visceral pain threshold is decreased indicating a visceral hypersensitivity. Consequently, this study was designed to evaluate the effect of injection of TNBS into the colon on visceral pain threshold in a experimental model of colonic distension.

Animals and Surgery

Male Sprague-Dawley rats (Janvier, Le Genest-St-Use, France) weighing 340–400 g are used. The animals are housed 3 per cage in a regulated environment (20±1° C., 50 ±5% humidity, with light 8:00 am to 8:00 pm). Under anesthesia (ketamine 80 mg/kg i.p; acepromazin 12 mg/kg ip), the injection of TNBS (50 mg/kg) or saline (1.5 mL/kg) is performed into the proximal colon (1 cm from the cecum). After the surgery, animals are individually housed in polypropylene cages and kept in a regulated environment (20±1° C., 50±5% humidity, with light 8:00 am to 8:00 pm) during 7 days.

Experimental Procedure

At Day 7 after TNBS administration, a balloon (5–6 cm length) is inserted by anus and kept in position (tip of balloon 5 cm from the anus) by taping the catheter to the base of the tail. The balloon is progressively inflated by step of 5 mm Hg, from 0 to 75 mm Hg, each step of inflation lasting 30 seconds. Each cycle of colonic distension is controlled by a standard barostat (ABS, St-Die, France). The threshold corresponds to the pressure which produced the first abdominal contraction and the cycle of distension is then discontinued. The colonic threshold (pressure expressed in mm Hg) is determined after performance of four cycles of distension on the same animal.

Determination of the Activity of the Compound

Data is analyzed by comparing test compound-treated group with TNBS-treated group and control group. Mean and sem are calculated for each group. The antiallodynic activity of the compound is calculated as follows:

$$\text{Activity (\%)} = (\text{group C} - \text{group T})/(\text{group A} - \text{group T})$$

Group C: mean of the colonic threshold in the control group

Group T: mean of the colonic threshold in the TNBS-treated group

Group A: mean of the colonic threshold in the test compound-treated group

Statistical Analysis

Statistical significance between each group was determined by using a one-way ANOVA followed by Student's unpaired t-test. Differences were considered statistically significant at $p < 0.05$.

Compounds

TNBS is dissolved in EtOH 30% and injected under a volume of 0.5 mL/rat. TNBS is purchased from Fluka.

Oral administration of the test compound or its vehicle is performed 1 hour before the colonic distension cycle.

Sub-cutaneous administration of the test compound or its vehicle is performed 30 minutes before the colonic distension cycle.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain. from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mglkg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the methods of preparing final products of Formula I above. They are not intended to limit the scope of the invention in any way.

EXAMPLE 1

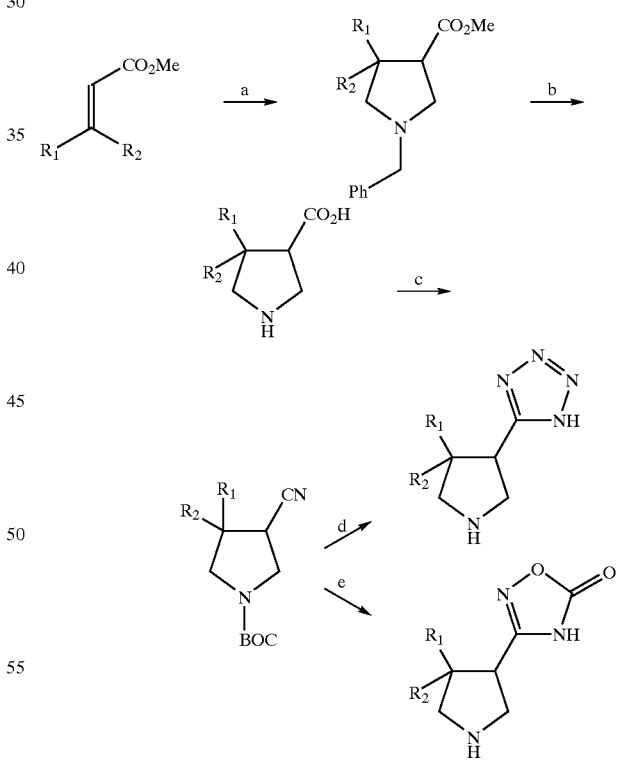

a) Me3SiCH$_2$N(Bz)CH$_2$OMe, TFA -78° C.;

b) i. H$_2$ Pd/C; ii. HCl;

c) i. BOC$_2$O, Et$_3$N; ii; Isobutyl chloroformate, Et$_3$N, NH3; iii. cyanuric chloride;

d) i. NaN$_3$ toluene reflux; ii. HCl;

e) i. NH2OH, EtOH; ii. CDI, Et$_3$N; iii. HCl.

Compounds that can be prepared by this method include, for example:

trans 3-(4-Isobutyl-pyrrolidin-3-yl)-4H-[1,2,4]oxadiazol-5-one;
cis 3-(4-Isobutyl-pyrrolidin-3-yl)-4H-[1,2,4]oxadiazol-5-one;
trans 5-(4-Isobutyl-pyrrolidin-3-yl)-1H-tetrazole;
cis 5-(4-Isobutyl-pyrrolidin-3-yl)-1H-tetrazole;
3-(2-Aza-spiro[4.5]dec-4-yl)-4H-[1,2,4]oxadiazol-5-one; and
4-(1H-Tetrazol-5-yl)-2-aza-spiro[4.5]decane.

What is claimed is:

1. A compound of formula

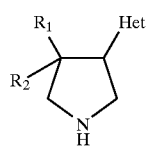

I or a pharmaceutically acceptable salt thereof wherein:

$R_1$ and $R_2$ are each independently hydrogen or a straight or branched alkyl of from 3 to 8 carbon atoms; or $R_1$ and $R_2$ are taken together with the carbon atom to which they are attached to form a carbocyclic ring of from 3 to 8 carbon atoms;

Het is a group selected from

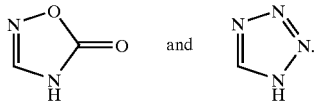

2. A compound according to claim 1 wherein $R_1$ and $R_2$ are each independently hydrogen or a straight or branched alkyl of from 3 to 8 carbon atoms; and Het is

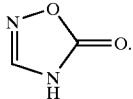

3. A compound according to claim 1 selected from: cis 3-(4-Isobutyl-pyrrolidin-3-yl)-4H-[1,2,4]oxadiazol-5-one and trans 5-(4-Isobutyl-pyrrolidin-3-yl)-4H-[1,2,4]oxadiazol-5-one.

4. A compound according to claim 1 wherein $R_1$ and $R_2$ are taken together with the carbon to which they are attached to form a carbocyclic ring of from 3 to 8 carbon atoms; and Het is

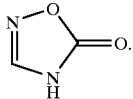

5. A compound according to claim 1 named 3-(2-Aza-spiro[4.5]dec-4-yl)-4H-[1,2,4]oxadiazol-5-one.

6. A compound according to claim 1 wherein $R_1$ and $R_2$ are each independently hydrogen or a straight or branched alkyl of from 3 to 8 carbon atoms; and Het is

7. A compound according to claim 1 and selected from trans 5-(4-Isobutyl-pyrrolidin-3-yl)-IH-tetrazole and cis 5-(4-Isobutyl-pyrrolidin-3-yl)-1H-tetrazole.

8. A compound according to claim 1 wherein $R_1$ and $R_2$ are taken together with the carbon atom to which they are attached to form a carbocyclic ring of from 3 to 8 carbon atoms; and Het is

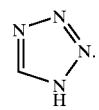

9. A compound according to claim 1 named 4-(1H-Tetrazol-5-yl)-2-aza-spiro[4.5]decane.

10. A pharmaceutical composition comprising a therapeutically effective amount of one or more compounds according to claim 1 and a pharmaceutically acceptable carrier.

11. A method for treating epilepsy comprising administering a therapeutically effective amount of a compound according to claim 1 to a mammal in need of said treatment.

12. A method for treating faintness attacks, hypokinesia, and cranial disorders comprising administering a therapeutically effective amount of a compound according to claim 1 to a mammal in need of said treatment.

13. A method for treating neurodegenerative disorders comprising administering a therapeutically effective amount of a compound according to claim 1 to a mammal in need of said treatment.

14. A method for treating depression comprising administering a therapeutically effective amount of a compound according to claim 1 to a mammal in need of said treatment.

15. A method for treating anxiety comprising administering a therapeutically effective amount of a compound according to claim 1 to a mammal in need of said treatment.

16. A method for treating panic comprising administering a therapeutically effective amount of a compound according to claim 1 to a mammal in need of said treatment.

17. A method for treating pain comprising administering a therapeutically effective amount of a compound according to claim 1 to a mammal in need of said treatment.

18. A method for treating neuropathological disorders comprising administering a therapeutically effective amount of a compound according to claim 1 to a mammal in need of said treatment.

19. A method for treating sleep disorders comprising administering a therapeutically effective amount of a compound according to claim 1 to a mammal in need of said treatment.

* * * * *